United States Patent

Bourrain et al.

[11] Patent Number: 5,998,416
[45] Date of Patent: Dec. 7, 1999

[54] PIPERAZINE, PIPERIDINE AND TETRAHYDROPYRIDINE DERIVATIVES AS 5-HT RECEPTOR AGONISTS

[75] Inventors: Sylvie Bourrain, Harlow; Angus Murray MacLeod, Bishops Stortford; Graham Andrew Showell, Welwyn Garden City; Leslie Joseph Street, Harlow, all of United Kingdom

[73] Assignee: Merck Sharp & Dohme Ltd., Hoddesdon, United Kingdom

[21] Appl. No.: 09/171,930

[22] PCT Filed: May 15, 1997

[86] PCT No.: PCT/GB97/01329

§ 371 Date: Oct. 26, 1998

§ 102(e) Date: Oct. 26, 1998

[87] PCT Pub. No.: WO97/45432

PCT Pub. Date: Dec. 4, 1997

[30] Foreign Application Priority Data

May 24, 1996 [GB] United Kingdom .................... 9610978

[51] Int. Cl.⁶ ...................... A61K 31/495; A61K 31/505; C07D 405/14

[52] U.S. Cl. ........................... 514/253; 514/254; 514/318; 514/333; 544/238; 544/295; 544/333; 544/357; 544/362; 544/364; 544/405; 546/194; 546/256

[58] Field of Search ..................................... 544/364, 295, 544/238, 357; 514/253, 254

[56] References Cited

FOREIGN PATENT DOCUMENTS

| 497512 | 8/1992 | European Pat. Off. |
| WO 94/02477 | 2/1994 | WIPO |
| WO 95/21166 | 8/1995 | WIPO |
| WO 95/28400 | 10/1995 | WIPO |
| 95 32196 | 11/1995 | WIPO |
| Wo 96/04274 | 2/1996 | WIPO |

*Primary Examiner*—Emily Bernhardt
*Attorney, Agent, or Firm*—James L. McGinnis; David L. Rose; Philippe L. Durette

[57] ABSTRACT

A class of N-substituted piperazine, piperidine, and tetrahydropyridine derivatives, further subltitutedat the 4-position by an optionally substituted alkenyl, alkynyl, aryl-alkyl or heteroaryl-alkyl moiety, are selective agonists of $5-HT_1$-like receptors, being potent agonists of the human $5-HT_{1D\alpha}$ receptor subtype whilst possessing at least a 10-fold selective affinity for the $5-HT_{1D\alpha}$ receptor subtype relative to the $5-HT_{1D\beta}$ subtype; they are therefore useful in the treatment and/or prevention of clinical conditions, in particular migraine and associated disorders, for which a subtype-selective agonist of $5-HT_{1D}$ receptors is indicated, whilst eliciting fewer side-effects, notably adverse cardiovascular events, than those associated with non-subtype-selective $5-HT_{1D}$ receptor agonists.

8 Claims, No Drawings

PIPERAZINE, PIPERIDINE AND TETRAHYDROPYRIDINE DERIVATIVES AS 5-HT RECEPTOR AGONISTS

The present invention relates to a class of substituted piperazine, piperidine and tetrahydropyridine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988. Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415: J. P. Ottervanger et al., *The Lancet*. 1993, 341. 861–2: and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666-9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

WO-A-94/08993 and WO-A-95/28400 describe substituted pyridinlbenzofuran derivatives, and analogues thereof These compounds are stated therein to be selective agonists at 5-HT$_1$-like receptors and thus useful in treating conditions associated with cephalic pain, including migraine. Neither of these publications, however, discloses or even suggests the substituted piperazine, piperidine and tetrahydropyridine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with an optionally substituted alkenyl, alkynyl, aryl-alkyl or heteroaryl-alkyl substituent; nor is there any suggestion therein that the range of substituents specified at the 5-position of the indole moiety might be successfully replaced by an optionally substituted six-membered heteroaromatic ring.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

WO-A-95/32196, WO-A-96/04269 and WO-A-96/04274 describe various classes of heterocyclic compounds as alpha subtype-selective agonists of the human 5-HT$_{1D}$ receptor. However, there is no disclosure or suggestion in any of these publications of the substituted six-membered heteroaromatic ring-containing compounds provided by the present invention.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype. Moreover, the compounds in accordance with this invention possess interesting properties in terms of their efficacy and/or bioavailability.

The present invention provides a compound of formula I, or a salt or prodrug thereof:

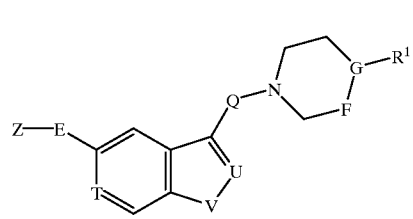

(I)

wherein

Z represents an optionally substituted six-membered heteroaromatic ring selected from pyridine, pyrazine, pyrimidine and pyridazine;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents nitrogen or CH;

U represents nitrogen or C—R$^2$;

V represents oxygen, sulphur or N—R3;

—F—G— represents —CH$_2$—N—, —CH$_2$—CH— or —CH=C—;

R$^1$ represents C$_{3-6}$ alkenyl, C3-6 alkynyl, aryl(C$_{1-6}$)alkyl or heteroaryl(C$_{1-6}$)alkyl, any of which groups may be optionally substituted; and R$^2$ and R$^3$ independently represent hydrogen or C$_{1-6}$ alkyl.

The six-membered heteroaromatic ring Z in the compounds of formula I above may be optionally substituted by one or more substituents, typically by one or two substituents. Examples of suitable substituents on the six-membered heteroaromatic ring Z include C$_{1-6}$ alkyl, C$_{2-6}$ alkenyl, C$_{2-6}$ alkynyl, C$_{3-7}$ cycloalkyl, aryl, aryl(C$_{1-6}$)alkyl, C$_{3-7}$ heterocycloalkyl, heteroaryl, heteroaryl(C$_{1-6}$)alkyl, halogen, halo(C$_{1-6}$)alkyl, cyano, cyano(C$_{1-6}$)alkyl, trifluoromethyl, and —(CH$_2$)$_n$—R$^4$, in which a is zero, 1, 2 or 3 (preferably zero or 1) and R$^4$ represents —OR$^a$, —OCOR$^c$, —OCO$_2$R$^a$, —SR$^a$, —SOR$^a$, —SO$_2$R$^c$, —CH=CHSO$_2$R$^c$, —SO$_2$NR$^a$R$^b$, —CH=CHSO$_2$NR$^a$R$^b$, —NR$^a$R$^b$, —NR$^a$COR$^c$, —NR$^a$CO(CH$_2$)$_b$OR$^d$ (in which b is 1 or 2, preferably 1), —NR$^a$CO$_2$R$^d$, —NR$^a$SO$_2$R$^c$, —NR$^d$CONR$^a$R$^b$, —NR$^d$SO$_2$NR$^a$R$^b$, —COR$^c$, —CH=CHCOR$^c$, —CO$_2$R$^a$, —CONR$^a$R$^b$, —CH=CHCONR$^a$R$^b$, or —CONR$^d$NR$^a$R$^b$, or R$^4$ represents a group of formula (a), (b), (c), (d) or (e):

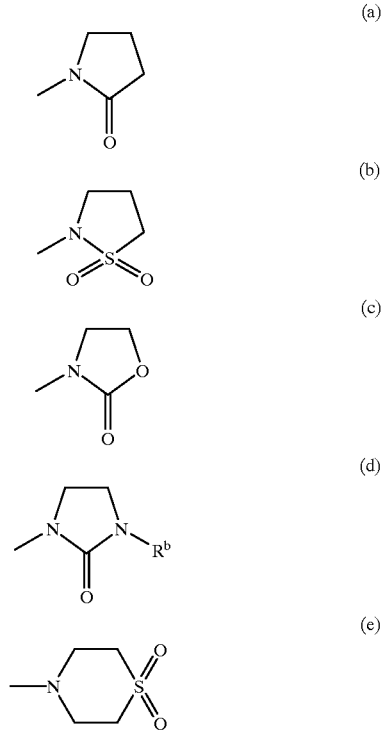

wherein R$^a$ and R$^d$ independently represent hydrogen, C$_{1-6}$ alkyl, trifluoromethyl, phenyl, fluorophenyl or tetrahydropyranyl; R$^b$ represents hydrogen, C$_{1-6}$ alkyl, trifluoromethyl, phenyl or fluorophenyl; and R$^c$ represents hydrogen, C$_{1-6}$ alkyl, trifluoromethyl, phenyl, fluorophenyl, tetrahydropyranyl, azetidinyl, pyrrolidinyl, piperidinyl or morpholinyl.

The group R$^1$ may be optionally substituted by one or more substituents. Where R$^1$ represents aryl(C$_{1-6}$ alkyl or heteroaryl(C$_{1-6}$)alkyl, any optional substitution will suitably be on the aryl or heteroaryl moiety thereof, although substitution on the alkyl moiety thereof is an alternative possibility. Examples of optional substituents on the group R$^1$ include halogen, cyano, trifluoromethyl, triazolyl, tetrazolyl, C$_{1-6}$ alkyl-tetrazolyl, hydroxy, C$_{1-6}$ alkoxy, C$_{1-6}$ alkylthio, C$_{2-6}$ alkoxycarbonyl, C$_{2-6}$ alkylcarbonyl, C$_{1-6}$ alkylsulphonyl, arylsulphonyl, amino, C$_{1-6}$ alkylamino, di(C$_{1-6}$)alkylamino, di(C$_{1-6}$)alkylaminomethyl, C$_{2-6}$ alkylcarbonylamino, arylcarbonylamino, C$_{2-6}$ alkoxycarbonylamino. N-(C$_{1-6}$)alkyl-N-(C$_{2-6}$)alkoxycarbonylamino, C$_{1-6}$ alkylsulphonylamino, arylsulphonylamino, C$_{1-6}$ alkylsulphonylaminomethyl, aminocarbonylamino, C$_{1-6}$ alkylaminocarbonylamino, di(C$_{1-6}$)alkylaminocarbonylamino. mono- or diarylaminocarbonylamino, pyrrolidinylcarbonylamino, piperidinylcarbonylamino, aminocarbonyl, C$_{1-6}$ alkylaminocarbonyl, di(C$_{1-6}$)alkylaminocarbonyl, aminosulphonyl, C$_{1-6}$ alkylaminosulphonyl, di(C$_{1-6}$ alkylaminosulphonyl, aminosulphonylmethyl, C$_{1-6}$ alkylaminosulphonylmethyl and di(C$_{1-6}$) alkylaminosulphonylmethyl.

As used herein, the expression "C$_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "C$_{1-6}$ alkoxy", "C$_{1-6}$ alkylthio" and "C$_{1-6}$ alkylamino" are to be construed accordingly.

The expression "C$_{2-6}$ alkenyl" as used herein refers to straight-chained and branched alkenyl groups containing from 2 to 6 carbon atoms. Typical examples include vinyl, allyl, dimethylallyl and butenyl groups.

The expression "C$_{2-6}$ alkynyl" as used herein refers to straight-chained and branched alkynyl groups containing from 2 to 6 carbon atoms. Typical examples include ethynyl and propargyl groups.

Typical C$_{3-7}$ cycloalkyl groups include cyclopropyl, cyclobutyl, cyclopentyl and cyclohexyl.

Typical aryl groups include phenyl and naphthyl.

The expression "aryl(C$_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, furyl. benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl(C$_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl. imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridinylpropyl, pyrimidinylmethyl, pyrazinylmethyl, quinolinylmethyl and isoquinolinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard. Elsevier, 1985.

Certain compounds according to the present invention may be capable of existing as tautomeric forms. For example, a hydroxypyridine derivative in accordance with the invention may exist in admixture with its tautomeric pyridinone isomer. It is to be understood that all possible tautomers and mixtures thereof in any proportion are encompassed within the scope of the present invention.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The optionally substituted six-membered heteroaromatic ring Z in formula I is suitably a substituted or unsubstituted pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl or pyridazin-4-yl ring, especially pyridin-3-yl, pyridin-4-yl or pyrimidin-5-yl, and in particular pyridin-3-yl or pyrimidin-5-yl.

The six-membered heteroaromatic ring Z is unsubstituted or substituted by one or more substituents, typically by one or two substituents. Examples of optional substituents which may typically be attached to the moiety Z include methyl, hydroxy, methoxy, methoxycarbonyl, methoxymethyl, aminomethyl, dimethylaminomethyl, acetylaminomethyl, benzoylaminomethyl, tert-butoxycarbonylaminomethyl, methylsulphonylaminomethyl, phenylsulphonylaminomethyl, aminocarbonylmethyl, ethyl, aminoethyl. acetylaminoethyl, benzoylaminoethyl, methoxycarbonylaminoethyl, ethoxycarbonylaminoethyl, tert-butoxycarbonylaminoethyl, methylsulphonylaminoethyl, aminocarbonylaminoethyl, methylaminocarbonylaminoethyl, tert-butylaminocarbonylaminoethyl, phenylaminocarbonylaminoethyl, pyrrolidinylcarbonylaminoethyl, cyclopropyl, phenyl, naphthyl, benzyl, phenylethyl, phenylpropyl, pyridinylmethyl, amino, methylamino, dimethylamino, aminocarbonyl, methylaminocarbonyl, azetidinylcarbonyl and pyrrolidinylcarbonyl.

Particular substituents which may be attached to the moiety Z include hydroxy, methoxy, methoxycarbonyl, methoxymethyl and methylsulphonyl-aminomethyl.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by one or more substituents selected from fluoro and hydroxy giving rise, for example, to a 2-hydroxypropylene, 2-hydroxymethyl-propylene, 2-fluoropropylene or 2-fluoromethyl-propylene chain Q. Moreover, E may represent a chemical bond such that the moiety Z is attached directly to the central fused bicyclic heteroaromatic ring system containing the variables T, U and V.

Suitably, E represents a chemical bond or a methylene linkage.

Representative alkylene chains for Q include propylene, butylene, 2-fluoropropylene, 2-hydroxypropylene and 2-hydroxymethyl-propylene. Suitably, Q represents a propylene linkage.

The compound of formula I in accordance with the present invention is suitably an indole, benzofuran or benzthiophene derivative of formula IA, an indazole derivative of formula IB, or a pyrrolo[2,3-c]pyridine derivative of formula IC:

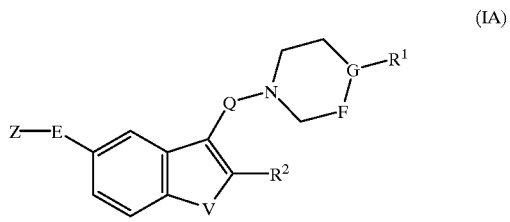

(IA)

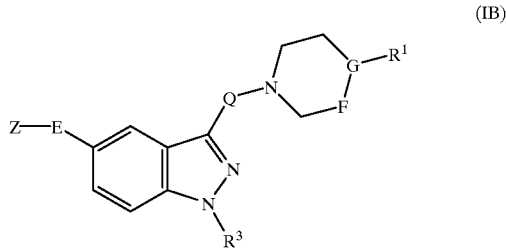

(IB)

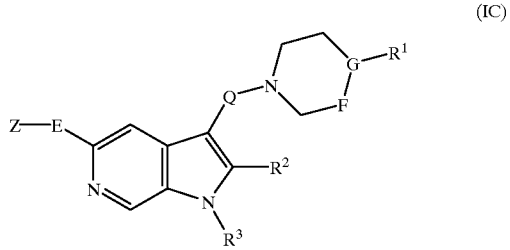

(IC)

wherein Z, E, Q, V, F, G, $R^1$, $R^2$ and $R^3$ are as defined above. Typically, the compounds according to the invention are indole or benzofuran derivatives of formula ID:

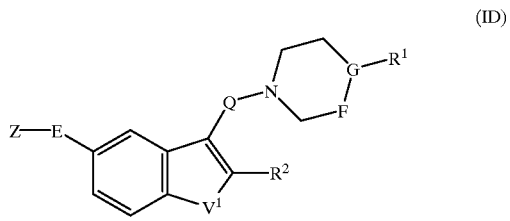

(ID)

wherein $V^1$ represents oxygen or N-$R^3$, and Z, E, Q, F, G, $R^1$, $R^2$ and $R^3$ are as defined above, in particular wherein $R^2$ and R3 are both hydrogen.

Suitable values for the substituent R1 include allyl, dimethylallyl, butenyl, propargyl, benzyl, phenylethyl, phenylpropyl, furylmethyl, thienylmethyl, imidazolylmethyl, pyridinylmethyl and pyridinylpropyl, any of which groups may be optionally substituted by one or more substituents selected typically from halogen, cyano, triazolyl, tetrazolyl, $C_{1-6}$ alkyl-tetrazolyl, $C_{1-6}$ alkoxy, amino, di($C_{1-6}$)alkylamino, di($C_{1-6}$)alkylaminomethyl, $C_{2-6}$ alkylcarbonylamino, $C_{2-6}$ alkoxycarbonylamino, N-($C_{1-6}$)alkyl-N-($C_{2-6}$)alkoxycarbonylamino, $C_{1-6}$ alkylsulphonylamino, aminocarbonylamino, aminocarbonyl, $C_{1-6}$ alkylaminocarbonyl, di($C_{1-6}$) alkylaminocarbonyl, aminosulphonyl and $C_{1-6}$ alkylaminosulphonylmethyl.

Representative values of $R^1$ include allyl, dimethylallyl, butenyl, propargyl, benzyl, fluorobenzyl, cyanobenzyl, tetrazolyl-benzyl, methyltetrazolyl-benzyl, methoxybenzyl, aminobenzyl, dimethylaminomethyl-benzyl, acetylaminobenzyl, aminocarbonyl-benzyl, methylaminocarbonyl-benzyl, dimethylaminocarbonyl-benzyl. aminosulphonyl-benzyl, phenylethyl, fluoro-phenylethyl, cyano-phenylethyl, triazolyl-phenylethyl, amino-phenylethyl, dimethylamino-phenylethyl, acetylamino-phenylethyl, methoxycarbonylamino-phenylethyl, (N-methyl-N-methoxycarbonyl)amino-phenylethyl, aminocarbonylamino-phenylethyl, phenylpropyl (especially 2-phenylpropyl), furylmethyl, thienylmethyl, imidazolylmethyl, pyridinylmethyl, amino-pyridinylmethyl and pyridinylpropyl (especially 2-(pyridin-2-yl)propyl).

Particular values of $R^1$ include fluoro-phenylethyl, phenylpropyl and pyridinylpropyl, especially 2-(3-fluorophenyl)ethyl, 2-phenylpropyl or 2-(pyridin-2-yl)propyl.

Suitably $R^2$ and $R^3$ independently represent hydrogen or methyl, especially hydrogen.

A particular sub-class of compounds according to the invention is represented by the compounds of formula IIA, and salts and prodrugs thereof:

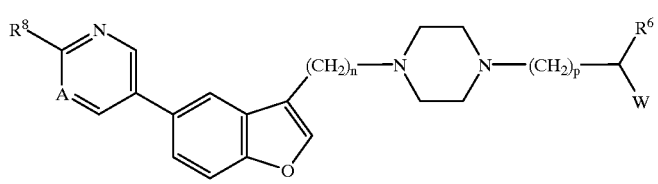

(IIA)

wherein n is 2, 3 or 4, preferably 3;

p is zero, 1 or 2;

A represents nitrogen or C-$R^5$;

$R^5$ represents hydrogen, $C_{2-4}$ alkoxycarbonyl, $C_{1-3}$ alkoxy($C_{1-3}$)alkyl or $C_{-3}$ alkylsulphonylamino($C_{1-3}$)alkyl;

$R^6$ represents hydrogen or $C_{1-3}$ alkyl;

W represents a group of formula (Wa), (Wb) or (Wc):

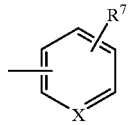

(Wa)

(Wb)

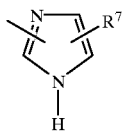

(Wc)

in which

X represents CH or nitrogen;

Y represents oxygen, sulphur, NH or N-methyl; and $R^7$ represents hydrogen, halogen, cyano, trifluoromethyl, $C_{1-6}$ alkoxy, $C_{2-6}$ alkylcarbonyl, amino, $C_{1-6}$ alkylamino, di($C_{1-6}$)alkvlamino, di($C_{1-6}$) alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl; and $R^8$ represents hydrogen, hydroxy or $C_{1-6}$ alkoxy.

Particular values of $R^5$ include hydrogen, methoxycarbonyl, methoxymethyl and methylsulphonylaminomethyl.

Suitably, $R^6$ represents hydrogen or methyl.

Particular values of $R^7$ include hydrogen, fluoro, cyano, methoxy, amino, dimethylaminomethyl, acetylamino, aminocarbonylamino, methylaminocarbonyl and aminosulphonyl, especially hydrogen or fluoro.

Suitable values of $R^8$ include hydrogen, hydroxy and methoxy. In a particular embodiment, $R^8$ is hydrogen.

Another sub-class of compounds according to the invention is represented by the compounds of formula IIB, and salts and prodrugs thereof.

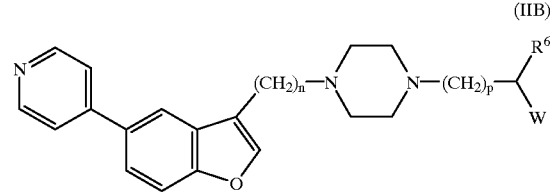

(IIB)

wherein n, p, $R^6$ and W are as defined with reference to formula IIA above.

Specific compounds within the scope of the present invention include:

5-[3-(3-(4-(2-(3-fluorophenyl)ethyl)piperazin-1-yl) propyl)benzofuran-5-yl]nicotinic acid methyl ester;

1-(2-phenylpropyl)-4-[3-(5-(pyridin-3-yl)benzofuran-3-yl)propyl]piperazine;

1-[3-(5-(5-methoxymethylpyridin-3-yl)benzofuran-3-yl) propyl]-4-(2-phenylpropyl)piperazine:
1-[3-(5-(pyridin-3-yl)benzofuran-3-yl)propyl]-4-[2-(pyridin-2-yl)propyl]piperazine;
5-[3-(3-(4-(2-phenylpropyl)piperazin-1-yl)propyl) benzofuran-5-yl]pyrimidine;
5-[3-(3-(4-(2-(pyridin-2-yl)propyl)piperazin-1-yl)propyl) benzofuran-5-yl]pyrimidine:
1-(2-phenylpropyl)-4-[3-(5-(pyridin-4-yl)benzofuran-3-yl)propyl]piperazine;
1-[3-(5-(6-methoxypyridin-3-yl)benzofuran-3-yl) propyl]-4-[2-(pyridin-2-yl)propyl]piperazine;
5-[3-(3-(4-(2-(pyridin-2-yl)propyl)piperazin-1-yl)propyl) benzofuran-5-yl]-1H-pyridin-2-one;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules. sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention. or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein —F—G— represents —$CH_2$—N— may be prepared by a process which comprises attachment of the $R^1$ moiety to a compound of formula III:

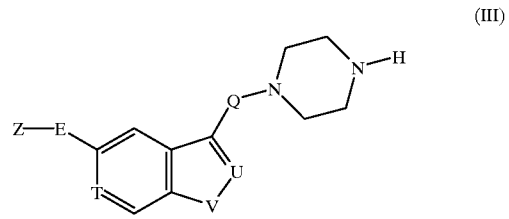

(III)

wherein Z, E, Q, T, U and V are as defined above; by conventional means including N-alkylation.

Attachment of the $R^1$ moiety to the compounds of formula III may conveniently be effected by standard alkylation techniques. One example thereof comprises treatment with an alkenyl halide such as 4-bromobut-1-ene, 4-bromo-2-methylbut-2-ene or allyl bromide, an alkynyl halide such as propargyl bromide, or an aryl($C_{1-6}$)alkyl or heteroaryl($C_{1-6}$)alkyl halide such as benzyl iodide, typically under basic conditions, e.g. sodium hydride or potassium carbonate in N,N-dimethylformamide, or triethylamine in acetonitrile. Another example comprises treatment of the compound of formula III with an aryl($C_{1-6}$)alkyl or heteroaryl($C_{1-6}$))alkyl mesylate such as 2-(4-cyanophenyl)ethyl methanesulphonate, typically in the presence of sodium carbonate and sodium iodide, in a suitable solvent such as 1,2-dimethoxyethane.

Alternatively, the $R^1$ moiety may conveniently be attached by reductive alkylation, which may be accomplished in a single step, or as a two-step procedure. The single-step approach suitably comprises treating the required compound of formula III as defined above with the appropriate aldehyde, e.g. benzaldehyde, furfuraldehvde or thiophene carboxaldehvde, in the presence of a reducing agent such as sodium cyanoborohydride. In a typical two-step procedure, for the preparation of a compound of formula I wherein $R^1$ corresponds to a group of formula —$CH_2R^{11}$, a carboxylic acid derivative of formula $R^{11}$—$CO_2H$ is condensed with the required compound of formula III, suitably in the presence of 1-(3-dimethylaminopropyl)-3-ethylcarboduimide hydrochloride and 1-hydroxybenzotriazole hydrate, to afford a compound corresponding to formula I wherein $R^1$ represents —$COR^{11}$; the carbonyl group thereof can hen be reduced, for example by treatment with diisobutylaluminium hydride, and the required compound of formula I thereby obtained.

The compounds of formula III above wherein T represents CH, U represents C—$R^2$ and V represents N—$R^3$, corresponding to the indole derivatives of formula ID as defined above wherein $V^1$ represents N—$R^3$, —F—G— represents —$CH_2$—N— and $R^1$ is hydrogen, may be prepared by a process which comprises reacting a compound of formula IV:

(IV)

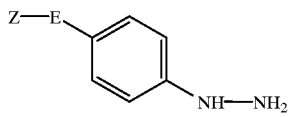

wherein Z and E are as defined above; with a compound of formula V, or a carbonyl-protected form thereof:

(V)

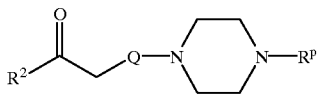

wherein $R^2$ and Q are as defined above, and $R^p$ represents an amino-protecting group; followed, where required, by N-alkylation by standard methods to introduce the moiety $R^3$; with subsequent removal of the amino-protecting group $R^p$.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives.

The protecting group RP in the compounds of formula V is suitably a carbamoyl moiety such as tert-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds IV and V may be carried out in a single step, or may proceed via an initial non-cyclising step at a lower temperature to give an intermediate of formula VI:

(VI)

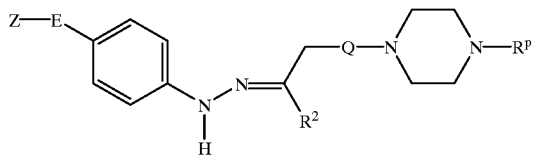

wherein Z, E, Q, $R^2$ and $R_p$ are as defined above; followed by cyclisation using a suitable reagent, e.g. a polyphosphate ester.

The intermediates of formula V, or carbonyl-protected forms thereof, may be prepared by reacting a compound of formula VII, or a carbonyl-protected form thereof, with a compound of formula VIII:

(VII)

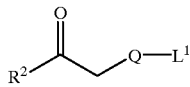

-continued (VIII)

wherein Q, $R^2$ and $R^p$ are as defined above, and $L^1$ represents a suitable leaving group.

The leaving group $L^1$ is suitably a halogen atom, e.g. chlorine or bromine.

Where $L^1$ represents a halogen atom, the reaction between compounds VII and VIII is conveniently effected by stirring the reactants under basic conditions in a suitable solvent, for example potassium carbonate in N,N-dimethylformamide, or triethylamine in tetrahydrofuran or acetonitrile.

The compounds according to the invention wherein T represents CH, U represents C—$R^2$ and V represents N—$R^3$—i.e. the indole derivatives of formula ID as defined above wherein VI represents N—$R^3$—may alternatively be prepared by a process which comprises reacting a compound of formula IV as defined above with a compound of formula IX, or a carbonyl-protected form thereof:

(IX)

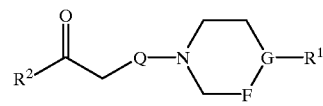

wherein Q, F, G, $R^1$ and $R^2$ are as defined above; under conditions analogous to those described above for the reaction between compounds IV and V: followed, where required, by N-alkylation by standard methods to introduce the moiety $R^3$.

As for the compounds of formula V, suitable carbonyl-protected forms of the compounds of formula IX include the dimethyl acetal or ketal derivatives. Where the alkylene chain Q is substituted by a hydroxy group, this group may condense with the carbonyl moiety in compounds V and IX, whereby the carbonyl moiety is protected in the form of a cyclic hemiacetal.

As with that between compounds IV and V, the Fischer reaction between compounds IV and IX may be carried out in a single step, or may proceed via an initial non-cyclising step at a lower temperature to give an intermediate of formula X:

(X)

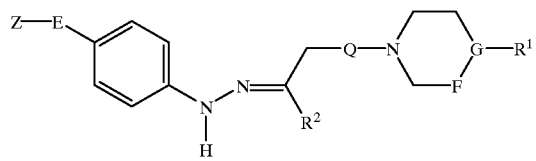

wherein Z, E, Q, F, G, $R^1$ and $R^2$ are as defined above; followed by cyclisation using a suitable reagent, e.g. a polyphosphate ester.

The intermediates of formula IX, or carbonyl-protected forms thereof, may be prepared by reacting a compound of formula VII as defined above, or a carbonyl-protected form thereof, with a compound of formula XI:

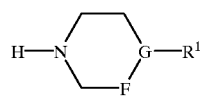

(XI)

wherein F, G and R¹ are as defined above; under conditions analogous to those described above for the reaction between compounds VII and VIII.

In an alternative procedure, the compounds of formula III above may be prepared by a process which comprises reacting a compound of formula VIII as defined above with a compound of formula XII:

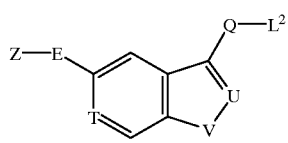

(XII)

wherein Z, E, Q, T, U and V are as defined above, and $L^2$ represents a suitable leaving group; followed by removal of the amino-protecting group $R^p$.

Similarly, the compounds of formula I as defined above may be prepared by a process which comprises reacting a compound of formula XI as defined above with a compound of formula XII as defined above.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compound XII and compound VIII or XI is conveniently carried out in a suitable solvent such as 1,2-dimethoxyethane or isopropyl alcohol, typically in the presence of a base such as sodium carbonate or potassium carbonate, optionally with the addition of sodium iodide.

In one representative approach, the compounds of formula XII wherein T and U both represent CH, V represents NH and $L^2$ represents a mesyloxy or tosyloxy group may be prepared by the sequence of steps illustrated in the following reaction scheme (cf. Larock and Yum. *J. Am Chem. Soc.*, 1991, 113, 6689):

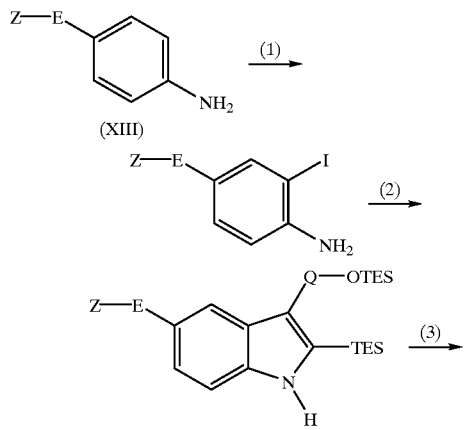

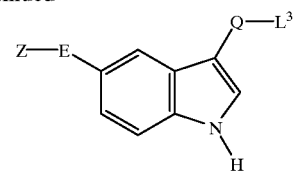

-continued wherein Z, E and Q are as defined above, $L^3$ represents mesyloxy or tosyloxy, and TES is an abbreviation for triethylsilyl.

In Step 1 of the reaction scheme, the aniline derivative XIII is treated with iodine monochloride, typically in methanol or acetonitrile, in order to introduce an iodine atom ortho to the amine moiety. Step 2 involves a palladium-mediated coupling reaction with the protected acetylene derivative TES—C≡C—Q—OTES, typically using palladium acetate and triphenylphosphine in the presence of lithium chloride and sodium carbonate, suitably in N,N-dimethylformamide at an elevated temperature. This is followed in Step 3 by removal of the TES moiety, typically by treatment with hydrochloric acid; followed in turn by mesylation or tosylation, suitably by using mesyl chloride or tosyl chloride respectively in the presence of a base such as triethylamine or pyridine, typically in dichloromethane/acetonitrile.

In another representative approach, the compounds of formula XII wherein T and U both represent CH, V represents NH, Q represents a propylene chain and $L^2$ represents a mesyloxy or tosyloxy group may be prepared by reacting 3,4-dihydro-2H-pyran with a compound of formula IV as defined above or a salt thereof, under a variant of the Fischer reaction conditions as described above for the reaction between compounds IV and V: followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by stirring the pyran derivative with an acid addition salt of the hydrazine derivative IV, typically the hydrochloride salt. in an inert solvent such as aqueous ethanol. The resulting hydrazide derivative can then be cyclised by treatment with a Lewis acid such as zinc chloride, in a solvent such as 1.2-dimethoxyethane, suitably at the reflux temperature of the solvent.

In another procedure, the compounds of formula III above wherein E represents a chemical bond may be prepared by reacting a compound of formula XIV with a compound of formula XV:

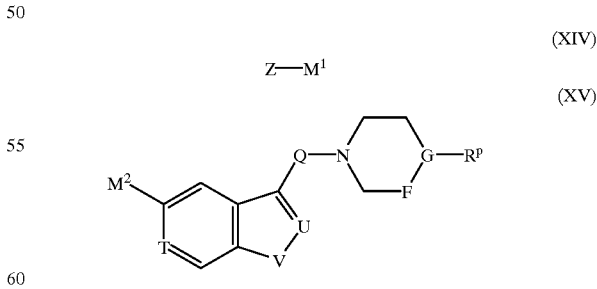

(XIV)

(XV)

wherein Z, Q, T, U, V, F, G and $R^p$ are as defined above; one of $M^1$ and $M^2$ represents a suitable leaving group, and the other represents a boronic acid moiety —B(OH)₂ or a $C_{1-4}$ alkyl ester or anhydride thereof; in the presence of a transition metal catalyst; followed by removal of the protecting group $R^p$.

Similarly, the compounds of formula I as defined above wherein E represents a chemical bond may be prepared by a process which comprises reacting a compound of formula XIV as defined above with a compound of formula XVI:

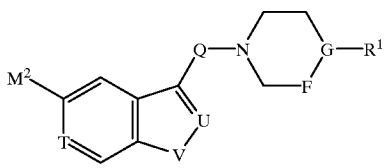

(XVI)

wherein Q, T, U, V, F, G, $R^1$ and $M^2$ are as defined above; in the presence of a transition metal catalyst.

The leaving group $M^1$ or $M^2$ is suitably a halogen atom, e.g. bromine.

The transition metal catalyst of use in the reaction between compound XIV and compound XV or XVI is suitably tetrakis-(triphenylphosphine)palladium (0). The reaction is conveniently carried out in an inert solvent such as aqueous 1,2-dimethoxyethane, advantageously in the presence of a base such as sodium acetate or sodium carbonate, typically at an elevated temperature.

In a further procedure, the compounds of formula III above wherein T represents CH, U represents nitrogen and V represents N—$R^3$, corresponding to the indazole derivatives of formula IB as defined above wherein —F—G— represents —$CH_2$—N— and $R^1$ is hydrogen, may be prepared by a process which comprises cyclising a compound of formula XVII:

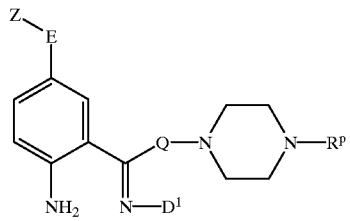

(XVII)

wherein Z, E, Q and $R^p$ are as defined above, and $D^1$ represents a readily displaceable group; followed, where required, by N-alkylation by standard methods to introduce the moiety $R^3$; with subsequent removal of the amino-protecting group $R^p$.

Similarly, the compounds of formula I wherein T represents CH, U represents nitrogen and V represents N—$R^3$— i.e. the indazole derivatives of formula IB as defined above—may be prepared by a process which comprises cyclising a compound of formula XVIII:

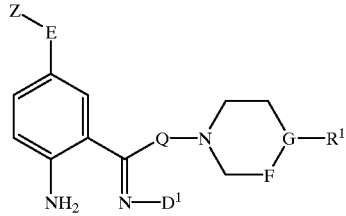

(XVIII)

in which Z, E, Q, F, G, $R^1$ and $D^1$ are as defined above; followed, where required, by N-alkylation by standard methods to introduce the moiety $R^3$.

The cyclisation of compounds XVII and XVIII is conveniently achieved in a suitable organic solvent at an elevated temperature, for example in a mixture of m-xylene and 2,6-lutidine at a temperature in the region of 140° C.

The readily displaceable group $D^1$ in the compounds of formula XVII and XVIII suitably represents a $C_{1-4}$ alkanoyloxy group, preferably acetoxy. Where $D^1$ represents acetoxy, the desired compound of formula XVII or XVIII may be conveniently prepared by treating a carbonyl compound of formula XIX:

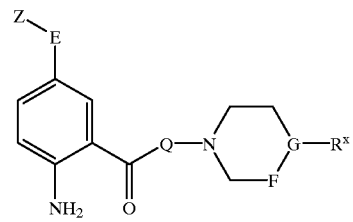

(XIX)

wherein Z, E, Q, F and G are as defined above, and $R^X$ corresponds to the group $R^1$ as defined above, or $R^X$ represents an amino-protecting group as defined for $R^p$ when —F—G— represents —$CH_2$—N—; or a protected derivative thereof, preferably the N-formyl protected derivative: with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XIX may conveniently be prepared by ozonolysis of the corresponding indole derivative of formula XX:

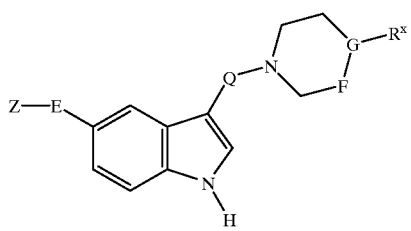

(XX)

wherein Z, E, Q, F, G and $R^X$ are as defined above; followed by a reductive work-up, advantageously using dimethylsulphide.

The indole derivatives of formula XX may be prepared by methods analogous to those described in the accompanying Examples, or by procedures well known from the art.

In a still further procedure, the compounds of formula III above wherein T represents CH, U represents C—$R^2$ and V represents oxygen or sulphur, corresponding to the benzofuran or benzthiophene derivatives of formula IA wherein V is oxygen or sulphur respectively, —F—G— represents —$CH_2$—N— and $R^1$ is hydrogen, may be prepared by a process which comprises cyclising a compound of formula XXI:

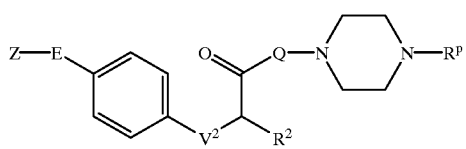

(XXI)

wherein Z, E, Q, $R^2$ and $R^p$ are as defined above, and $V^2$ represents oxygen or sulphur; followed by removal of the amino-protecting group $R^p$.

Similarly, the compounds of formula I wherein T represents CH, U represents $C-R^2$ and V represents oxygen or sulphur—i.e. the benzofuran or benzthiophene derivatives of formula IA above—may be prepared by a process which comprises cyclising a compound of formula XXII:

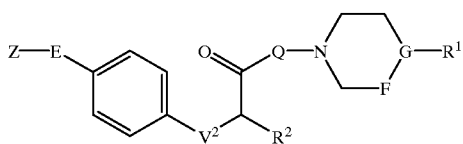

(XXII)

wherein Z, E, Q, F, G, $R^1$, $R^2$ and $V^2$ are as defined above.

The cyclisation of compounds XXI and XXII is conveniently effected by using polyphosphoric acid or a polyphosphate ester, advantageously at an elevated temperature.

The compounds of formula XXI and XXII may be prepared by reacting a compound of formula XXIII with a compound of formula XXIV:

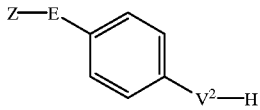

(XXIII)

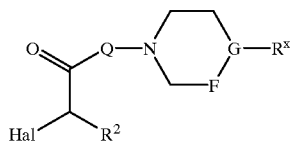

(XXIV)

wherein Z, E, Q, F, G, $R^2$, $V^2$ and $R^x$ are as defined above, and Hal represents a halogen atom.

The reaction is conveniently effected in the presence of a base such as sodium hydroxide.

In a yet further procedure, the compounds of formula III above may be prepared by a process which comprises reducing a compound of formula XXV:

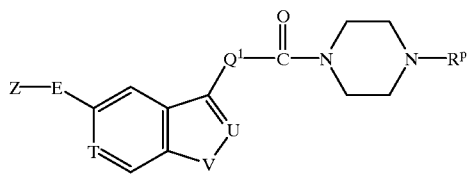

(XXV)

wherein Z, E, T, U, V and $R^p$ are as defined above, and —$Q^1$—$CH_2$— corresponds to the moiety Q as defined above; with subsequent removal of the amino-protecting group $R^p$.

Similarly, the compounds according to the invention may be prepared by a process which comprises reducing a compound of formula XXVI:

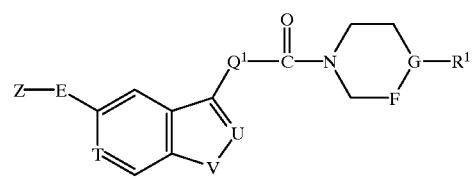

(XXVI)

wherein Z, E, T, U, V, F, G, $R^1$ and $Q^1$ are as defined above.

The reduction of compounds XXV and XXVI is conveniently effected by treating the appropriate compound with a reducing agent such as lithium aluminium hydride in an appropriate solvent, e.g. diethyl ether or tetrahydrofuran, or mixtures thereof.

The compounds of formulae XXV and XXVI above may suitably be prepared by reacting a compound of formula XXVII with the appropriate compound of formula XXVIII:

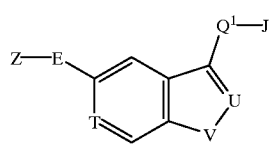

(XXVII)

(XXVIII)

wherein Z, E, T, U, V, F, G, $R^x$ and $Q^1$ are as defined above, and J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XXVII above wherein J is an acid chloride moiety may be prepared by treating the corresponding carboxylic acid derivative with thionyl chloride in toluene. Similarly, the intermediates of formula XXVII wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula XXVIII.

In one additional procedure, the compounds of formula III above may be prepared by a process which comprises reacting a compound of formula VIII as defined above with a compound of formula XXIX:

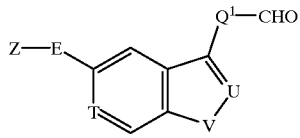

(XXIX)

wherein Z, E, T, U, V and $Q^1$ are as defined above; in the presence of a reducing agent: followed by removal of the protecting group $R^p$.

Similarly, the compounds of formula I as defined above may be prepared by a process which comprises reacting a compound of formula XI as defined above with a compound of formula XXIX as defined above; in the presence of a reducing agent.

Moreover, the compounds of formula XV above may be prepared by reacting a compound of formula VIII as defined above with a compound of formula XXX:

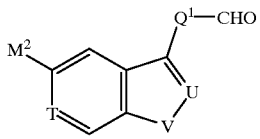

(XXX)

wherein T, U, V, $M^2$ and $Q^1$ are as defined above; in the presence of a reducing agent.

Similarly, the compounds of formula XVI above may be prepared by reacting a compound of formula XI as defined above with a compound of formula XXX as defined above; in the presence of a reducing agent.

A suitable reducing agent for use in conjunction with the above reaction between compound VIII or XI and compound XXIX or XXX is sodium triacetoxyborohydride, in which case the reaction is conveniently effected in the presence of acetic acid and a solvent such as dichloromethane.

The compounds of formula XXIX and XXX may be prepared by reduction of the appropriate compound of formula XXXI:

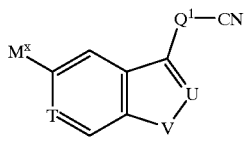

(XXXI)

wherein T, U, V and $Q^1$ are as defined above: and $M^x$ corresponds to the moiety Z-E- as defined above, or Mx corresponds to the group of formula $M^2$ as defined above.

A suitable reducing agent for effecting the transformation of the cyano moiety in compound XXXI to the carboxaldehyde (CHO) moiety in compounds XXIX and XXX is diisobutylaluminium hydride (DIBAL-H), and the reaction is conveniently carried out in a solvent such as dichloromethane.

A representive approach to the nitrile intermediates of formula XXXI in which T and U both represent CH, V is oxygen and $Q^1$ is an ethylene linkage can be illustrated as follows:

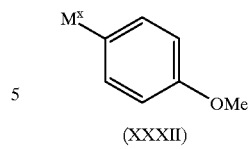

(XXXII)

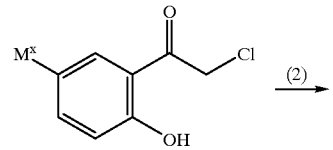

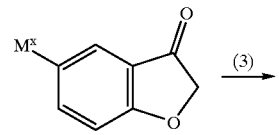

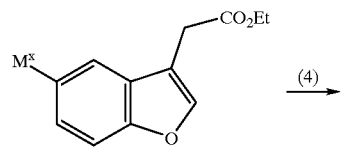

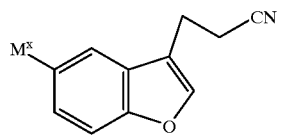

in which $M^x$ is as defined above.

In Step 1, the anisole derivative XXXII is treated with chloroacetyl chloride in the presence of aluminium chloride, whereby the methoxy substituent is demethylated, with concomitant introduction of the chloroacetyl moiety ortho to the resulting phenolic OH. This compound is then cyclised in Step 2, by treatment with methanolic sodium acetate at an elevated temperature. Step 3 comprises treatment of the resulting furanone derivative with triethyl phosphonoacetate in the presence of a strong base such as potassium hexamethyldisilazide, followed in Step 4 by DIBAL-H reduction of the ethyl ester moiety in the resulting compound. The hydroxyethyl benzofuran derivative thereby obtained is mesylated. and the mesyl group thereof subsequently displaced by cyanide ion, to afford the desired cyanoethyl benzofuran analogue.

The intermediates of formula XV above may suitably be prepared by reacting a compound of formula VIII as defined above with a compound of formula XXXIII:

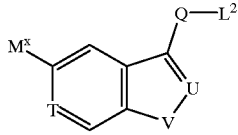

(XXXIII)

wherein Q, T, U, V, $L^2$ and $M^2$ are as defined above: under conditions analogous to those described above for the reaction between compounds VIII and XII.

Similarly, the intermediates of formula XVI above may be prepared by reacting a compound of formula XI as defined above with a compound of formula XXXIII as defined above, under conditions analogous to those described above for the reaction between compounds XI and XII.

Typical intermediates of formula XXXIII, wherein T and U are both CH, V is oxygen, Q is an ethylene linkage and L² is mesyl or tosyl, can be prepared from compound XXXII, in which $M^x$ corresponds to the group $M^2$, by following Steps 1 to 3 of the reaction scheme illustrated immediately above to obtain the ethyl ester intermediate, which can then be reduced with DIBAL-H and mesylated or tosylated under standard conditions.

Where they are not commercially available, the starting materials of formula IV, VII, VIII, XI, XIII, XIV, XXIII, XXIV, XXVII, XXVIII and XXXII may be prepared by methods analogous to those described in the accompanying Examples, or by standard procedures well known from the art.

It will be understood that any compound of formula I initially obtained from any of the above processes may, where appropriate. subsequently be elaborated into a further compound of formula I by techniques known from the art. For example, a compound of formula I wherein —F—G— represents —CH=C— initially obtained may be readily converted into the corresponding compound wherein —F—G— represents —CH$_2$—CH— by conventional catalytic hydrogenation procedures. In addition, a compound of formula I wherein $R^1$ is benzyl initially obtained may be converted by catalytic hydrogenation to the corresponding compound of formula III, which in turn may be converted into a further compound of formula I using standard N-alkylation techniques as described above. Furthermore, a compound of formula I initially obtained wherein the $R^1$ moiety is substituted by nitro or cyano may be converted by catalytic hydrogenation to the corresponding amino- or aminomethyl-substituted compound respectively. Additionally, a compound of formula I wherein the $R^1$ moiety is substituted by hydroxy, possibly obtained by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the $R^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be transesterified, by treatment with the appropriate alcohol in the presence of a mineral acid such as sulphuric acid; or saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiimide hydrochloride and 1-hydroxybenzotriazole. A compound of formula I initially obtained wherein the Z or $R^1$ moiety is substituted by $C_{1-6}$ alkoxy, e.g. methoxy, may be converted into the corresponding hydroxy-substituted analogue by treatment with boron tribromide, typically in dichloromethane. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in N,N-dimethylformamide.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it mav be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-HT$_{1D\alpha}$ receptor subtype, inhibit forskolin-stimulated adenylyl cyclase activity, and stimulate [$^{35}$S]-GTPγS binding to membranes from clonal cell lines expressing human cloned receptors.

5-HT$_{1D\alpha}$/5-HT$_{1D\beta}$ Radioligand Binding

Chinese hamster ovary (CHO) clonal cell lines expressing the human 5-HT$_{1D\alpha}$ and 5-HT$_{1D\beta}$ receptors were harvested in PBS and homogenised in ice cold 50 mM Tris-HCl (pH 7.7 at room temperature) with a Kinematica polytron and centrifuged at 48,000g at 4° C. for 11 min. The pellet was then resuspended in 50 mM Tris-HCl followed by a 10 min incubation at 37° C. Finally the tissue was recentrifuged at 48,000g, 4° C. for 11 min and the pellet resuspended, in assay buffer (composition in mM: Tris-HCl 50, pargyline 0.01, CaCl$_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GFIB filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which IC$_{50}$ (the molar concentration of compound necessary to inhibit binding by 50%) values could be calculated for each test compound. The IC$_{50}$ values for binding to the 5-HT$_{1D\alpha}$ receptor subtype obtained for the compounds of the accompanying Examples were below 50 nM in each case. Furthermore, the compounds of the accompanying Examples were all found to possess a selective affinity for the 5-$HT_{1D\alpha}$ receptor subtype of at least 10-fold relative to the 5-$HT_{1D\beta}$ subtype.

5-$HT_{1D\alpha}$/5-$HT_{1D\beta}$ Adenylyl Cyclase Assay

Studies were performed essentially as described in *J. Pharmacol. Exp. Ther.*, 1986, 238, 248. CHO clonal cell lines expressing the human cloned 5-$HT_{1D\alpha}$ and 5-$HT_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of $\alpha$-[$^{33}$P]-ATP to [$^{33}$P]-cyclic AMP. A 10 $\mu$l aliquot of the membrane suspension was incubated, for 10–15 min, in a final volume of 50 $\mu$l, at 30° C., with or without forskolin (10 $\mu$M), in the presence or absence of test compound. The incubation buffer consisted of 50 mM Tris HCl (pH 7.6 at room temperature), 100 mM NaCl, 30 $\mu$M GTP, 50 $\mu$M cyclic AMP, 1 mM dithiothreitol, 1 mM ATP, 5 mM $MgCl_2$, 1 mM EGTA. 1 mM 3-isobutyl-1-methylxanthine, 3.5 mM creatinine phosphate, 0.2 mg/ml creatine phosphokinase, 0.5–1 $\mu$Ci $\alpha$-[$^{33}$P]-ATP and 1 nCi [$^3$H]-cyclic AMP. The incubation was initiated by the addition of membrane, following a 5 min preincubation at 30° C., and was terminated by the addition of 100 $\mu$l SDS (composition in mM: sodium lauryl sulphate 2%, ATP 45, cyclic AMP 1.3, pH 7.5 at room temperature). The ATP and cyclic AMP were separated on a double column chromatography system (*Anal. Biochein.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

5-$HT_{1D\alpha}$/5-$HT_{1D\beta}$ GTP$\gamma$S Binding

Studies were performed essentially as described in *Br. J. Pharmacol.*, 1993, 109, 1120. CHO clonal cell lines expressing the human cloned 5-$HT_{1D\alpha}$ and 5-$HT_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA. pH 7.4 at room temperature and recentrifuged at 40,000 g. 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 $\mu$g protein/ml for the 5-$HT_{1D\alpha}$ receptor transfected cells and 40–50 $\mu$g protein/ml for the 5-$HT_{1D\beta}$ receptor transfected cells. The membrane suspension was then incubated, in a volume of 1 ml, with GDP (100 $\mu$M for 5-$HT_{1D\alpha}$ receptor transfected cells, 30 $\mu$M for the 5-$HT_{1D\beta}$ receptor transfected cells) and test compound at 30° C. for 20 min and then transferred to ice for a further 15 min. [$^{35}$S]-GTP$\gamma$S was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

EXAMPLE 1

5-[3-(3-(4-(2-(3-Fluorophenyl)ethyl)piperazin-1-yl)propyl)benzofuran-5-vl]nicotinic acid methyl ester 2 hydrogen oxalate Step 1: 1-(5-Bromo-2-hydroxyphenyl)-2-chloroethanone To a solution of 4-bromoanisole (17.4 ml, 138 mmol) in dichloromethane (150 ml) was added chloroacetyl chloride (32 ml, 400 mmol) followed by aluminium chloride (60 g, 450 mmol) keeping the temperature below 30° C. The yellow solution was heated to reflux for 8 hours, cooled down to ambient temperature, then ice water was added very carefully. The organic layer was separated and the aqueous extracted once with dichloromethane. The combined organics were dried (sodium sulphate) then evaporated to give an oil which was purified by crystallisation from hexane. The title compound was obtained as a yellow solid (18 g, 52%), mp 80–82° C. $^1$H NMR (250MHz, $CDCl_3$) $\delta$4.69 (2H, s), 6.95 (1H, d, J=9 Hz), 7.60 (1H, dd, J=1 and 9 Hz), 7.80 (1H, d, J=2 Hz), 11.60 (1H, s).

Step 2: 5-Bromobenzofuran-3-one

To a solution of the foregoing ethanone (18 g, 72 mmol) in methanol (150 ml) was added sodium acetate (7g, 85 mmol). The solution was heated at 65° C. for 1 hour, then the methanol was evaporated. The residue was partitioned between dichloromethane and water. The organic layer was separated and the aqueous solution reextracted once with dichloromethane. The combined organics were dried (sodium sulphate) then evaporated to give a gum which was purified by column chromatography on alumina using dichloromethane to afford a solid (5.6 g, 36%), mp 102–106° C. $^1$H NMR (250 MHz, $CDCl_3$) $\delta$4.67 (2H, s), 7.04 (1H, d, J=9 Hz), 7.69 (1H, dd, J=2 and 9 Hz), 7.79 (H, d, J=2 Hz).

Step 3: (5-Bromobenzofuran-3-yl)acetic acid ethyl ester

To a solution of triethyl phosphonoacetate (6 ml, 30.2 mmol) in dry tetrahydrofuran (200 ml) at −78° C. was added a solution of potassium bis(trimethylsilyl)amide in toluene (58 ml of a 0.5 M solution). After stirring for 2 hours at −78° C., 5-bromobenzofuran-3-one (5.5 g, 26 mmol) was added dropwise. The resulting solution was stirred 1 hour at −78° C. and overnight at room temperature. Saturated aqueous ammonium chloride solution and ethyl acetate were added. The organic layer was separated and evaporated to dryness to give the crude title compound which was purified by column chromatography on silica using chloromethane, followed by column chromatography on alumina using dichloromethane. (5-Bromobenzofuran-3-yl)acetic acid ethyl ester was obtained as a low melting solid (4.2 g, 57%), mp 38–40° C. $^1$H NMR 250 MHz, CDCl$_3$) δ1.28 (3H, t, J=7 Hz), 3.65 (2H, d, J=1 Hz), 4.20 (2H, q, J=7 Hz), 7.36 (1H, s), 7.38 (1H, d, J=2 Hz), 7.63 (1H, s), 7.71 (1H, d, J=2 Hz).

Step 4: 2-(5-Bromobenzofuran-3-yl)ethanol

To a solution of the foregoing ester (2.2 g, 7.8 mmol) in toluene (150 ml) under nitrogen at 5° C. was added diisobutylaluminium hydride in toluene (20 ml of a 1M solution). The solution was stirred 1 hour at 5° C. and 1 hour at ambient temperature, then methanol was added slowly followed by 10% aqueous potassium carbonate solution. The organic layer was decanted and the aqueous reextracted with ethyl acetate. The combined organics were filtered and evaporated to dryness to give the title compound (1.8 g, 96%) as an oil. $^1$H NMR (360 MHz, d$_6$-DMSO) δ2.78 (2H, dt, J=1 and 7 Hz), 3.68 (2H, dt, J=5 and 7 Hz), 4.73 (1H, t, J=5 Hz), 7.43 (1H, dd, J=2 and 9 Hz), 7.53 (1H, d, J=9 Hz), 7.84 (1H, s), 7.88 (1H, d, J=2 Hz).

Step 5: 3-(5-Bromobenzofuran-3-yl)propionitrile

To a solution of the foregoing alcohol (1.8 g, 7.5 mmol) in dichloromethane (30 ml) at −5° C. under nitrogen was added triethylamine (1.65 ml, 11.9 mmol) followed by methanesulphonyl chloride (0.86 ml, 11.2 mmol). The solution was stirred for 2 hours at −5° C., then washed twice with water, dried (sodium sulphate) and evaporated to give the mesylate which was redissolved in toluene (70 ml). Tetrabutylammonium cyanide was added (3 g, 11.2 mmol) and the solution heated to reflux for 1 hour. Water and ethyl acetate were added and the organic layer was separated, washed with water and evaporated. The residue was purified by column chromatography on silica using dichloromethane to give the title compound (1.6 g, 85%), mp 56–58° C. $^1$H NMR (250 MHz, CDCl$_3$) δ2.72 (2H, t, J=7 Hz), 3.03 (2H, t, J=7 Hz), 7.37 (1H, d, J=9 Hz), 7.43 (1H, dd, J=2 and 9 Hz), 7.59 (1H, s), 7.64 (1H, d, J=2 Hz).

Step 6: 1-(4-Benzylpiperazin-1-yl)-2-(3-fluorophenyl) ethanone

1-Benzylpiperazine (8g, 45.4 mmol), 3-fluorophenyl acetic acid (7.7 g, 50 mmol), triethylamine (7 ml, 50.6 mmol) and 1-(3-dimethylaminopropyl)-3-ethylcarbodiimide hydrochloride (9.6 g, 50 mmol) were stirred together in dry dichloromethane (150 ml) for 24 hours. The volatiles were evaporated then the residue was partitioned between ethyl acetate (200 ml) and saturated aqueous sodium hydrogen carbonate. The organic layer was separated, washed with brine, dried then evaporated. The residue was purified by column chromatography on silica using 2% methanol in dichloromethane→10% methanol in dichloromethane. The title compound was obtained as a yellow oil (11.1 g, 77%). δ (250 MHz, CDCl$_3$) 2.28 (2H, t, J=5 Hz), 2.42 (2H, t, J=5 Hz), 3.43 (2H, t, J=5 Hz), 3.44 (2H, s), 3.65 (2H, t, J=5 Hz), 3.71 (2H, s), 6.90–7.37 (9H, m).

Step 7: 1-[2-(3-Fluoroohenyl)ethyl]piperazine

The foregoing amide (11.0 g, 35.2 mmol) in anhydrous tetrahydrofuran (100 ml) was treated with lithium aluminium hydride (71 ml of a 1M tetrahydrofuran solution, 71 mmol) under a nitrogen atmosphere. After stirring for 1 hour at room temperature the reaction mixture was heated at reflux for 1 hour. The reaction mixture was cooled, water (2.7 ml) was cautiously added, followed by 15% sodium hydroxide (2. 7 ml) then further water (8 ml). After stirring for 1 hour the mixture was filtered and the solids washed through with 10% methanol in dichloromethane. The organic solution was evaporated to give 1-benzyl-4-[2-(3-fluorophenyl)ethyl]piperazine as a yellow oil (9 g, 85%). This piperazine (9 g, 30.2 mmol) in methanol (150 ml) was treated with ammonium formate (12 g, 152 mmol) and 20% palladium hydroxide on carbon (900 mg) under a nitrogen atmosphere. The mixture was stirred whilst heating at reflux for 4 hours, cooled, filtered then evaporated and the residue purified by column chromatography on silica using dichloromethane/methanol/ammonia (80:8:1). The title compound was obtained as a pale yellow oil (4.0 g, 63%). δ (360 MHz, CDCl$_3$) 2.50 (4H, br s), 2.59 (2H, t, J=7 Hz), 2.80 (2H, t, J=7 Hz), 2.93 (4H, t, J=5 Hz), 6.85–7.31 (4H, m).

Step 8: 1-[3-(5-Bromobenzofuran-3-yl)propyl]-4-[2-(3-fluorophenyl)ethyl]piperazine To a solution of the propionitrile from Step 5 (770 mg, 3.1 mmol) in dry dichloromethane (100 ml) at −40° C. under nitrogen was added diisobutylaluminium hydride in dichloromethane (6.4 ml of a 1M solution). The solution was stirred for 20 minutes at −40° C., then methanol was added followed by 10% aqueous potassium carbonate at −20° C. The organic layer was separated and the aqueous reextracted once with dichloromethane. The combined organics were dried (sodium sulphate) and cooled down to 5° C. before adding the amine from Step 7 (666 mg, 3.2 mmol) followed by sodium acetoxyborohydride (1.02 g, 4.8 mmol) and glacial acetic acid (0.5 ml, 8.7 mmol). The mixture was stirred 30 minutes at 5° C. and 30 minutes at room temperature. 10% aqueous potassium carbonate was added, the organic layer decanted and the aqueous reextracted once with dichloromethane. The combined organics were dried (sodium sulphate), evaporated and the residue purified by column chromatography on silica using a methanol/dichloromethane gradient. The title compound was obtained as an oil (1.15 g, 84%). The oxalate salt had mp 238–240° C. $^1$H NMR (360 MHz, d$_6$-DMSO) δ1.90–2.02 (2H m), 2.68 (2H, t, J=7 Hz), 2.75–2.96 (10H, m), 2.96–3.20 (4H, m), 6.99–7.16 (3H, m) 7.28–7.39 (1H, m), 7.45 (1H, dd, J=2 and 9 Hz), 7.54 (1H, d, J=9 Hz), 7.88 (1H, s). 7.89 (1H, d, J=2 Hz). MS, m/z 445 and 447 for (M+H)$^+$. (Found: C, 52.25; H, 4.99: N, 4.51. C$_{23}$H$_{26}$BrFN$_2$O.2 (CO$_2$H)$_2$ requires C, 51.85; H, 4.83; N, 4.45%).

Step 9: 5-[3-(3-(4-(2-(3-Fluorophenyl)ethyl)piperazin-1-yl) propyl)benzofuran-5-yl]boronic acid To a solution of the foregoing 5-bromobenzofuran (1.1 g, 2.5 mmol) in dry tetrahydrofuran (40 ml) at −78° C. under nitrogen was added sec-butyllithium in cyclohexane (3 ml of a 1.3M solution). After 30 minutes triisopropyl borate (1.15 ml, 5 mmol) was added and the solution allowed to warm to room temperature. The solution was stirred overnight, water added, and the solvent removed. The residue was azeotroped with ethanol and used crude.

Step 10: 5-[3-(3-(4-(2-(3-Fluorophenyl)ethyl)piperazin-1-yl)propyl)benzofuran-5-yl]nicotinic acid methyl ester 2 hydrogen oxalate To a solution of the crude boronic acid in ethylene glycol dimethyl ether (20 ml) was added ethyl 5-bromonicotinate (690 mg, 3 mmol) followed by sodium carbonate in water (5 ml of a 1M solution) and tetrakis(triphenylphosphine) palladium (0) (100 mg). The mixture was stirred at reflux for 18 hours, then a 1M aqueous solution of sodium carbonate was added. The mixture was extracted twice with ethyl acetate. The combined organics were dried (sodium sulphate), evaporated and the residue purified by column chromatography on silica using an ammonia/methanol/dichloromethane gradient. The nicotinic acid obtained was treated with concentrated sulphuric acid (0.3 ml) in methanol (20 ml) at reflux for 20 hours to give the title compound after purification by column chromatography on silica using a methanol/dichloromethane gradient. The oxalate salt had mp 218–219° C.

$^1$H NMR (360 MHz, d$_6$-DMSO) δ1.96–2.09 (2H m), 2.72–2.97 (10H, m), 2.97–3.16 (4H, mn), 3.94 (3H, s), 6.99–7.15 (3H m), 7.30–7.39 (1H, m), 7.68–7.76 (2H m), 7.91 (1H, s), 8.09 (1H, s), 8.54 (1H, d, J=2 Hz), 9.08 (1H, d, J=2 Hz), 9.20 (1H, d, J=2 Hz). MS, m/z 502 for (M+H)$^+$. (Found: C, 59.05; H 5.45; N, 5.96. $C_{30}H_{32}FN_3O_3$.2($CO_2H$)$_2$.½$H_2O$ requires C, 59.13; H, 5.40; N, 6.08%).

EXAMPLE 2

1-(2(RS)-Phenylpropyl)-4-[3-(5-(pyridin-3-yl) benzofuran-3-yl)propyl]piperazine 2.75 hydrogen oxalate Step 1: 4-(2(RS)-Phenylpropyl)piperazine-1-carboxylic acid t-butyl ester Piperazine-1-carboxylic acid t-butyl ester (10 g, 54 mmol), 2-henylpropionaldehyde (7.94 g, 59 mmol) in methanol (200 ml) were treated with glacial acetic acid (21.5 ml, 376 mmol), cooled to 0° C., then treated portionwise with sodium cyanoborohydride (3.72 g, 59 mmol). The reaction mixture was stirred at 0° C. for 30 minutes then at room temperature for 18 hours. The volatiles were evaporated then the residue basified with aqueous potassium carbonate and extracted with ethyl acetate (300 ml). The organic layer was dried (sodium sulphate) and the solvent evaporated to give a colourless oil. This oil was purified by column chromatography on silica using dichloromethane/methanol (97:3) to give the product as a colourless oil (11.87, 73%), δ (250 MHz, $CDCl_3$) 1.27 (3H, d, J=7 Hz), 1.45 (9H, s), 2.25–2.48 (6H, m), 2.90–2.96 (1H, m), 3.38 (4H, t, J=5 Hz), 7.15–7.33 (5H, m). MS, ES$^+$, m/z=305 for (M+H)$^+$.

Step 2: 1-(2(RS)-Phenyloroyoyl)piperazine

The foregoing piperazine (11.8 g, 39 mmol) was cooled to 0° C. then treated with 90% formic acid (25 ml). The solution was allowed to warm to room temperature and stirred for 18 hours. The volatiles were evaporated. the residue basified with aqueous potassium carbonate solution and extracted with ethyl acetate (2×100 ml). The combined organics were dried (sodium sulphate) then evaporated and the crude product purified by column chromatography on silica using dichloromethanelmethanol/ammonia (80:8:1) to give the title compound as a pale yellow oil (6.73 g, 5%), δ(250 MHz, $CDCl_3$) 1.27 (3H, d, J=7 Hz), 2.32–2.50 (6H, m), 2.78–3.01 (5H, m), 7.15–7.33 (5H, m).

Step 3: 1-[3-(5-Bromobenzofuran-3-yl)propyl]-4-(2(RS)-phenylpropyl)1227 piperazine The title compound was obtained following the procedure described in Example 1 Step 8 using the amine from Example 2 Step 2. The oxalate salt had mp 227–228° C. $^1$H NMR (360 MHz, d$_6$-DMSO) δ 1.19 (3H, d, J=7 Hz), 1.89–2.03 (2H, m), 2.50–2.90 (10H, m), 2.90–3.20 (7H, m), 7.15–7.3 (5H, m), 7.45 (1H, dd, J=2 and 9 Hz), 7.55 (1H, d, J=9 Hz), 7.88 (2H, s). MS, m/z 441 and 443 for (M+H)$^+$. (Found: C, 53.91; H, 5.35; N, 4.44. $C_{24}H_{29}BrN_2O$.2($CO_2H$)$_2$ requires C, 54.11; H, 5.35; N, 4.51%).

Step 4: 1-(2(RS)-Phenylpropyl)-4-[3-(5-(pyridin-3-yl)-benzofuran-3-yl)Propyl]piperazine 2.75 hydrogen oxalate To a solution of the foregoing 5-bromobenzofuran (100 mg, 0.23 mmol) in ethylene glycol dimethyl ether (10 ml) was added 3-pyridyl boronic acid (36 mg, 0.3 mmol) (Tarashima M. et al., Japan. Chem. Phar. Bull. 1983, 31(12), 4573), sodium acetate (65 mg, 0.61 mmol) and water (5 ml). The solution was purged with nitrogen for 2 hours. Tetrakis (triphenylphosphine)palladium (0) (200 mg) was added and the mixture stirred for 2 hours at reflux. After cooling down to ambient temperature, 10% aqueous sodium carbonate was added and the mixture extracted twice with ethyl acetate. The combined organics were washed with brine, dried (sodium sulphate) and evaporated. The residue was purified by column chromatography on silica using an ammonia/methanol/dichloromethane gradient. The title compound was obtained as an oil (80 mg, 80%). The hydrogen oxalate salt had mp 216–218° C. $^1$H NMR (360 MHz, d$_6$-DMSO) δ1.19 (3H, d, J=7 Hz), 1.98–2.10 (2H, m), 2.48–2.90 (10H, m), 2.90–3.29 (7H, m), 7.15–7.32 (5H, m), 7.47–7.53 (1H, m), 7.64–7.71 (2H, m), 7.90 (1H, s), 7.99 (1H, s), 8.13 (1H, d, J=8 Hz), 8.58 (1H, d, J=5 Hz), 8.96 (1H, s). MS, m/z 440 for (M+H)$^+$. (Found: C, 60.46; H, 5.76; N, 6.23. $C_{29}H_{33}N_3O$.2.75($CO_2H$)$_2$ requires C, 60.30; H, 5.65; N, 6.11%).

EXAMPLE 3

1-[3-(5-(5-Methoxymethylpyridin-3-yl)benzofuran-3-yl)propyl]-4-[2(RS)-phenylpropyl]piperazine 2.9 hydrogen oxalate Step 1: 5-Methoxymethylpyridin-3-ylboronic acid To a solution of n-butyl lithium in hexane (6 ml of a 1.6M solution) in diethyl ether (40 ml) at −100° C. under nitrogen was added dropwise 3-bromo-5-methoxymethylpyridine (1.2 g, 6 mmol) (WO 95/28400) in diethyl ether (20 ml). After stirring for 45 minutes at −100° C., trimethyl borate (1.1 ml, 9.8 mmol) was added and the reaction mixture stirred at −100° C. for an extra 75 minutes. Water was added followed by 4N aqueous sodium hydroxide when the temperature reached 10° C. The aqueous layer was decanted, acidified to pH 5 with 2N aqueous hydrochloric acid and extracted 5 times with dichloromethane. The combined organics were dried (sodium sulphate) and evaporated to give the title compound as an oil (100 mg, 10%). MS, m/z 168 for (M+H)$^+$. Rf 0.05 in ammonia/methanol/dichloromethane (1/10/90) on silica plate.

Step 2: 1-[3-(5-(5-Methoxvmethylpyridin-3-yl)benzofuran-3-yl)propyl]-4-[2(RS)-phenylpropyl]piperazine 2.9 hydrogen oxalate The title compound was obtained following the procedure described in Example 2 Step 4 using the 5-bromobenzofuran from Example 2 Step 3 and 5-methoxymethylpyridin-3-ylboronic acid. The hydrogen oxalate had mp 197–199° C. $^1$H NMR (360 MHz, d$_6$-DMSO) δ1.19 (3H, d, J=7 Hz). 2.00–2.10 (2H, m), 2.56–2.82 (8H, m), 2.94–3.20 (7H, m), 3.36 (3H, s), 4.55 (2H, s), 7.17–7.32 (5H, m), 7.68 (2H, s), 7.89 (1H, s), 7.99 (1H, s), 8.04 (1H. s), 8.51 (1H, s), 8.88 (1H, s). MS, m/z=484 for (M+H)$^+$. (Found: C, 59.33; H, 5.93; N, 5.67. $C_{31}H_{37}N_3O_2$. 2.9($CO_2H$)$_2$ requires C, 59.34; H, 5.79: N, 5.64%).

EXAMPLE 4

1-[-3-(5-(Pyridin-3-yl)benzofuran-3-yl)propyl]-4-[2(RS)-(pyridin-2-yl)-propyl]piperazine 3 hydrogen oxalate Step 1: 4-[2-(Pyridin-2-yl)propyl]piperazine-1-carboxylic acid t-butyl ester To a solution of 2-(pyridin-2-yl)propan-1-ol (Dutta, Sakti P., Achryya, Auditi K., Basu, Uma P., J. Indian Chem. Soc., 1966, 43(8), 549) (5.2 g, 37.9 mmol) in tetrahydrofuran (70 ml) at 0° C. was added triethylamine (5.8 ml, 41.7 mmol) followed by methanesulphonyl chloride (3.29 ml, 41.7 mmol). The solution was stirred for 1 hour at 0° C., diluted with 50% aqueous sodium hydrogen carbonate and extracted 3 times with ethyl acetate. The combined organics was washed with brine, dried (sodium sulphate) and evaporated to give the mesylate which was redissolved in isopropanol (60 ml). Potassium carbonate (5.67 g, 41.7 mmol) was added followed by piperazine-1-carboxylic acid t-butyl ester (14 g. 75.8 mmol) and the solution heated to reflux for 48 hours.

The solvent was evaporated and the residue dissolved in ethyl acetate. The organic solution was washed successively with water and brine, dried (sodium sulphate) and evaporated to give the title compound which was purified by column chromatography on silica using 5% methanol in dichloromethane as eluent (4.4 g, 38%). $^1$H NMR (250 MHz, CDCl$_3$) δ1.30 (3H, d. J=7 Hz), 1.44 (9H, s), 2.32–2.43 (4H, m), 2.49–2.62 (1H, m), 2.65–2.80 (1H m) 3.06–3.22 (1H, m), 3.32–3.42 (1H, m), 7.10–7.20 (2H, m), 7.56–7.66 (1H m), 8.50–8.58 (1H, m).

Step 2: 1-[2-(Pyridin-2-yl)propyl]piperazine

The foregoing piperazine (4.3 g, 14.1 mmol) was dissolved in methanol (50 ml) and hydrochloric acid gas was bubbled through for 5 minutes. After standing 1 hour the solvent was evaporated and the residue recrystallised from ethyl acetate. The title compound (free base) was obtained by eluting the hydrochloride salt through a DOWEX 50X8-200 column with ammonia/water/methanol 3/50/50 (2 g, 70%). $^1$H NMR (250 MHz, d$_6$-DMSO) δ1.17 (3H, d, J=7 Hz), 2.18–2.68 (10H, m), 3.03–3.21 (1H, m), 7.13–7.28 (2H, m), 7.63–7.72 (1H, m), 8.43–8.50 (1H, m).

Step 3: 1-[3-(5-Bromobenzofuran-3-yl)propyl]-4-[2(RS)-(pyridin-2-yl)propyl]piperazine The title compound was obtained following the procedure described in Example 1 Step 8 using the foregoing amine. $^1$H NMR (250 MHz, CDCl$_3$) δ1.30 (3H, d, J=7 Hz), 1.74–1.92 (2H, m), 2.31–2.76 (12H, m), (2H, t, J=7 Hz), 3.06–3.20 (1H, m), 7.05–7.20 (2H, m), 7.26–7.42 (3H, m), 7.53–7.65 (1H, m), 7.68 (1H, d, J=2 Hz), 8.72–8.80 (1H, m). MS, m/z=442 and 444 for (M+H)$^+$.

Step 4: 1-[3-(5-(Pyridin-3-yl)benzofuran-3-yl)propel-4-[2(RS)-(pyridin-2-yl)propyl]piperazine 3 hydrogen oxalate The title compound was obtained following the procedure described in Example 2 Step 4. The hydrogen oxalate had mp 165–170° C. $^1$H NMR (360 MHz, d$_6$-DMSO) δ1.20 (3H, d, J=7 Hz), 1.98–2.09 (2H, m), 2.56–2.87 (8H, m), 2.92–3.22 (7H, m), 7.18–7.25 (1H, m), 7.29 (1H, d, J=8 Hz), 7.48–7.52 (1H, m), 7.67 (1H, s), 7.66–7.74 (2H, m), 7.89 (1H, s), 7.99 (1H, s), 8.12 (1H dd, J=2 and 8 Hz), 8.49 (1H, d, J=4 Hz), 8.57 (1H. d, J=4 Hz), 8.95 (1H d, J=2 Hz). MS, m/z=441 for (M+H)$^+$. (Found C, 57.28: H, 5.48; N, 8.01. C$_{28}$H$_{32}$N$_4$O. 3(CO$_2$H)$_2$ requires C, 57.46; H, 5.39; N, 7.88%).

EXAMPLE 5

5-[3-(3-(4-(2(RS)-Phenylpropyl)piperazin-1-yl)propyl)benzofuran-5-yl]pyrimidine 2 hydrogen oxalate The title compound was obtained following the procedure described in Example 2 Step 4 using the 5-bromobenzofuran from Example 2 Step 3 and 5-pyrimidineboronic acid (S. Gronowitz et al., Chemica Scripta, 1986, 6, 305). The hydrogen oxalate had mp 216–219° C. $^1$H NMR (250 MHz, d$_6$-DMSO) δ1.19 (3H, d, J=7 Hz), 1.95–2.14 (2H, m), 2.52–3.24 (15H, m), 7.13–7.33 (5H, m), 7.70–7.80 (2H, m), 7.92 (1H, s), 8.11 (1H, s), 9.19 (1H, s), 9.21 (2H, s). MS, m/z=441 for (M+H)$^+$. (Found C, 62.56; H, 5.78; N, 8.72. C$_{28}$H$_{32}$N$_4$O. 2(CO$_2$H)$_2$ requires C, 61.93; H, 5.85; N, 9.03%).

EXAMPLE 6

5-[3-(3-(4-(2(R,S)-(Pyridin-2-yl)propyl)piperazin-1-yl)propyl)benzofuran-5-yl]pyrimidine 2.5 hydrogen oxalate The title compound was obtained following the procedure described in Example 2 step 4 using the 5-bromobenzofuran from Example 4 step 3 and 5-pyrimidine boronic acid. The hydrogen oxalate had mp 183–185° C. $^1$H NMR (360 MHz, d$_6$-DMSO) δ1.19 (3H, d, J=7 Hz), 1.96–2.09 (2H, m), 2.60–2.86 and 2.95–3.22 (15H, m), 7.21 (1H, dd, J=6 and 7 Hz), 7.29 (1H, d, J=8 Hz), 7.65–7.77 (3H, m), 7.90 (1H, s), 8.10 (1H, s), 8.49 (1H, d, J=7 Hz), 9.19 (1H, s), 9.20 (2H, s). MS, m/z=442 for (M+H)$^+$. (Found C, 57.12; H, 5.51; N, 10.51. C$_{27}$H$_{31}$N$_5$O. 2.5 (CO$_2$H)$_2$. 0.25H$_2$O requires C, 57.27;1 H, 5.48; N, 10.43%).

EXAMPLE 7

1-(2(R,S)-Phenylpropyl)-4-[3-(5-(pyridin-4-yl)benzofuran-3-yl)propyl]piperazine 3 hydrogen oxalate The title compound was obtained following the procedure described in Example 2 step 4 using the 5-bromobenzofuran from Example 2 step 3 and 4-pyridine boronic acid. The hydrogen oxalate had mp 216–218° C. $^1$H NMR (500 MHz, d$_6$-DMSO) δ1.19 (3H, d, J=7 Hz), 1.98–2.10 (2H, m), 2.48–3.25 (15H, m), 7.13–7.32 (5H, m), 7.71 (1H, d, J=8.5 Hz), 7.75 (1H, dd, J=8 and 2 Hz), 7.77 (2H, d, J=6 Hz), 7.91 (1H, s), 8.09 (1H, d, J=2 Hz), 8.64 (2H, d, J=6 Hz). MS, m/z=440 for (M+H)$^+$.

EXAMPLE 8

1-[3-(5-(6-Methoxypyridin-3-yl)benzofuran-3-yl)proyvl]-4-[2(R,S)-(pyridin-2-yl)propyl]piperazine 2 hydrogen oxalate The title compound was obtained following the procedure described in Example 2 step 4 using the 5-bromobenzofuran from Example 4 step 3 and 6-methoxypyridin-3-ylboronic acid (obtained following the procedure described in Example 3 step 1). The hydrogen oxalate had mp 198–200° C. $^1$H NMR (360 MHz, d$_6$-DMSO) δ1.20 (3H, d, J=7 Hz), 1.96–2.09 (2H, m), 2.55–2.86 and 2.95–3.24 (15H, m), 3.91 (3H, s), 6.95 (1H, d, J=8 Hz), 7.21 (1H, dd, J=6 and 7 Hz), 7.30 (1H, d, J=8 Hz), 7.58 (1H, d, J=8 Hz), 7.64 (1H, d, J=8 Hz), 7.68–7.76 (1H, m), 7.87 (1H, s), 8.07 (1H, dd. J=8 and 2 Hz), 8.50 (1H, d, J=8 Hz), 8.52 (1H, d, J=2 Hz). MS, m/z=472 for (M+H)$^+$. (Found C, 59.30; H, 5.65; N, 7.93. C$_{29}$H$_{34}$N$_4$O$_2$. 2.25(CO$_2$H)$_2$ requires C, 58.98; H, 5.84; N, 8.21%).

EXAMPLE 9

5-(3-(3-(4-(2(R,S)-(Pyridin-2-yl)propyl)piperazin-1-yl)propyl)benzofuran-5-yl]-1H-pyridin-2-one 3 hydrogen oxalate To a solution of the foregoing methoxy pyridine (100 mg 0.21 mmol in dichloromethane (10 ml) at 0° C. under nitrogen was added boron tribromide in dichloromethane (1.1 ml of a 1M solution). After stirring overnight at room temperature 5 ml of boron tribromide in dichloromethane was added and the mixture stirred for 48 hours. The mixture was cooled down to 0° C., diluted carefully with methanol and evaporated. The residue was purified by column chromatography on silica using ammonia/methanol/dichloromethane gradient to afford the title compound (21 mg, 22%). The hydrogen oxalate had mp>162° C. decomp. $^1$H NMR (360 MHz, d$_6$-DMSO) δ1.20 (3H, d, J=7 Hz), 1.91–2.07 (2H, m), 2.46–3.24 (15H, m), 6.47 (1H, d, J=9 Hz), 7.21 (1H, dd, J=6 and 7 Hz), 7.29 (1H, d, J=8 Hz), 7.48 (1H, dd, J=8 and 2 Hz), 7.57 (1H, d, J=8 Hz), 7.68–7.76 (2H, m), 7.78 (1H, d, J=2 Hz), 7.83 (1H, s), 7.88 (1H, dd, J=8 and 2 Hz), 8.49 (1H, d, J=8 Hz). MS, m/z=457 for (M+H)⁺. (Found C, 53.81; H, 5.62: N, 7.69. $C_{28}H_{32}N_4O_2 \cdot 3(CO_2H)_2 \cdot H_2O$ requires C, 53.75; H, 5.17; N, 7.37%).

We claim:

1. A compound of formula I, or a pharmaceutically acceptable salt thereof:

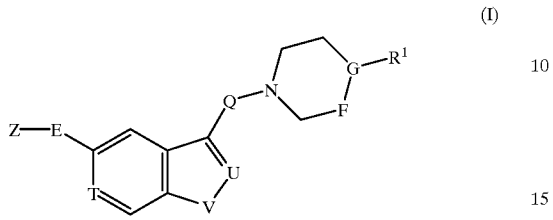

(I)

wherein

Z represents a six-membered heteroaromatic ring selected from pyridine, pyrazine, pyrimidine and pyridazine, optionally substituted with one or two substituents selected from hydroxy, $C_{1-6}$alkoxy, methoxycarbonyl, methoxymethyl, and methylsulphonylaminomethyl;

E represents a chemical bond or a straight or branched alkylene chain having from 1 to 4 carbon atoms;

Q represents a straight or branched alkylene chain having from 1 to 6 carbon atoms, optionally substituted in any position by one or more substituents selected from fluoro and hydroxy;

T represents CH;

U represents C—$R^2$;

V represents oxygen;

—F—G— represents —$CH_2$—N—;

$R^1$ represents $C_{3-6}$ alkenyl, $C_{3-6}$ alkynyl, phenyl($C_{1-6}$) alkyl, naphthyl($C_{1-6}$)alkyl or heteroaryl($C_{1-6}$)alkyl, wherein heteroaryl represents, furyl, thienyl, pyrrolyl, N-methyl pyrrolyl, or imidazolyl pyridinyl, any of which groups may be optionally substituted with one or two substituents selected from halogen, cyano, trifluoromethyl, $C_{2-6}$ alkylcarbonyl, triazolyl, tetrazolyl, $C_{1-6}$ alkyl-tetrazolyl, $C_{1-6}$ alkoxy, amino, di($C_{1-6}$)alkylamino, di($C_{1-6}$)alkylaminomethyl, $C_{2-6}$ alkylcarbonylamino, $C_{2-6}$ alkoxycarbonylamino, N-($C_{1-6}$ alkyl-N-($C_{2-6}$)alkoxycarbonylamino, $C_{1-6}$ alkylsulphonylamino, aminocarbonylamino, aminocarbonyl, $C_{1-6}$ alkylaminocarbonyl, di($C_{1-6}$) alkylaminocarbonyl, aminosulphonyl, and $C_{1-6}$ alkylaminosulphonylmethyl; and $R^2$ and $R^3$ independently represent hydrogen or $C_{1-6}$ alkyl.

2. A compound as claimed in claim 1 represented by formula IIA, and pharmaceutically acceptable salts thereof:

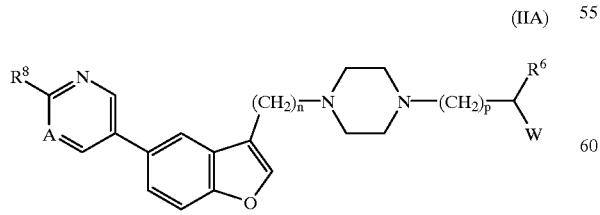

(IIA)

wherein n is 2, 3 or 4;

p is zero, 1 or 2;

A represents nitrogen or C—$R^5$;

$R^5$ represents hydrogen, $C_{2-4}$ alkoxycarbonyl, $C_{1-3}$ alkoxy ($C_{1-3}$)alkyl or $C_{1-3}$ alkylsulphonylamino($C_{1-3}$)alkyl;

$R^6$ represents hydrogen or $C_{1-3}$ alkyl;

W represents a group of formula (Wa), (Wb) or (Wc):

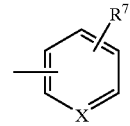

(Wa)

(Wb)

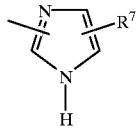

(Wc)

in which

X represents CH or nitrogen;

Y represents oxygen, sulphur, NH or N-methyl; and $R^7$ represents hydrogen, halogen, cyano trifluoromethyl, $C_{1-6}$ alkoxy, $C_{2-6}$ alkylcarbonyl, amino, $C_{1-6}$ alkylamino, di($C_{1-6}$)alkylamino, di($C_{1-6}$) alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl; and R8 represents hydrogen, hydroxy or $C_{1-6}$ alkoxy.

3. A compound as claimed in claim 2 wherein $R^8$ is hydrogen.

4. A compound as claimed in claim 1 represented by formula IIB, and pharmaceutically acceptable salts thereof:

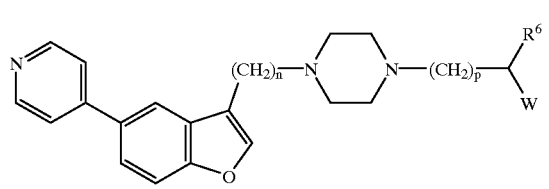

(IIB)

wherein n is 2,3 or 4;

p is zero, 1 or 2;

$R^6$ represents hydrogen or $C_{1-3}$ alkyl;

W represents a group of formula (Wa), (Wb) or (Wc):

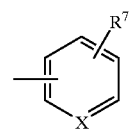

(Wa)

-continued

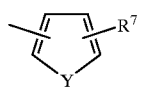
(Wb)

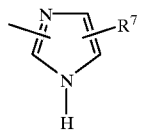
(Wc)

in which

X represents CH or nitrogen;

Y represents oxygen, sulphur, NH or N-methyl; and

R[7] represents hydrogen, halogen, cyano, trifluoromethyl, $C_{1-6}$ alkoxy, $C_{2-6}$ alkylcarbonyl, amino, $C_{1-6}$ alkylamino, di($C_{1-6}$)alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

5. A compound selected from:

5-[3-(3-(4-(2-(3-fluorophenyl)ethyl)piperazin-1-yl)propyl)benzofuran-5-yl]nicotinic acid methyl ester;

1-(2-phenylpropyl)-4-[3-(5-(pyridin-3-yl)benzofuran-3-yl)propyl]piperazine;

1-[3-(5-(5-methoxymethylpyridin-3-yl)benzofuran-3-yl)propyl]-4-(2-phenylpropyl)piperazine;

1-[3-(5-(pyridin-3-yl)benzofuran-3-yl)propyl]-4-[2-(pyridin-2-yl)propyl]piperazine;

5-[3-(3-(4-(2-phenylpropyl)piperazin-1-yl)propyl)benzofuran-5-yl]pyrimidine:

and pharmaceutically acceptable salts thereof.

6. A compound selected from:

5-[3-(3-(4-(2-(pyridin-2-yl)propyl)piperazin-1-yl)propyl)benzofuran-5-yl]pyrimidine;

1-(2-phenylpropyl)-4-[3-(5-(pyridin-4-yl)benzofuran-3-yl)propyl]piperazine;

1-[3-(5-(6-methoxypyridin-3-yl)benzofuran-3-yl)propyl]-4-[2-(pyridin-2-yl)propyl]piperazine;

5-[3-(3-(4-(2-(pyridin-2-yl)propyl)piperazin-1-yl)propyl)benzofuran-5-yl]-1H-pyridin-2-one;

and pharmaceutically acceptable salts thereof.

7. A pharmaceutical composition comprising a compound of formula I as defined in claim 1 or a pharmaceutically acceptable salt thereof in association with a pharmaceutically acceptable carrier.

8. A method for the treatment of migraine, cluster headache, chronic paroxysmal hemicrania, headache associated with vascular disorders, tension headache, and paediatric migraine, which method comprises administering to a patient in need of such treatment an effective amount of a compound of formula I as defined in claim 1 or a pharmaceutically acceptable salt thereof.

* * * * *